United States Patent [19]

Anaebonam et al.

[11] Patent Number: 4,853,416

[45] Date of Patent: Aug. 1, 1989

[54] SOLUTIONS OF PENTAMIDINE

[75] Inventors: Aloysius Anaebonam, Brookline; Emmett Clemente, Manchester; Theresa Devlin, Brighton; Diane Ringden, Somerville, all of Mass.

[73] Assignee: Fisons Corporation, Leicestershire, England

[21] Appl. No.: 185,463

[22] Filed: Apr. 25, 1988

[51] Int. Cl.$^4$ ........................................ A61K 31/155
[52] U.S. Cl. ................................................ 514/636
[58] Field of Search ...................................... 514/636

[56] References Cited

PUBLICATIONS

Chemical Abstracts 105: 85051b (1986).
Chemical Abstracts 107: 53x (1987).

*Primary Examiner*—Jerome D. Goldberg

*Attorney, Agent, or Firm*—Marshall, O'Toole, Gerstein, Murray & Bicknell

[57] ABSTRACT

A pharmaceutical composition comprising an aqueous solution of pentamidine or a pharmaceutically acceptable salt thereof, the solution having a pH of less than 4.5. The pH of the solution is preferably less than 4.0, more preferably less than 3.5, and especially less than 3.0.

Also disclosed is a method for the prophylactic or remedial treatment of pneumo-cystis carinii pneumonia, which method comprises administration by inhalation to a patient having or being susceptible to that condition of a therapeutically effective quantity of an aqueous solution of pentamidine, or a pharmaceutically acceptable salt thereof, the solution having a pH of less than 4.5.

18 Claims, No Drawings

SOLUTIONS OF PENTAMIDINE

CASE 3822001

SOLUTIONS OF PENTAMIDINE

This invention relates to pharmaceutical compositions, in particular to aqueous solutions of pentamidine.

BACKGROUND TO THE INVENTION 1,5-Di(4-amidinophenoxy)pentane, which is generically known as pentamidine, has for many years been known for use as a pharmaceutical, in particular for the treatment of the early stages of African trypanosomiasis ('sleeping sickness'). Pentamidine has also been found to be effective in the treatment of pneumo-cystis carinii pneumonia (PCP), a condition which is commonly contracted by patients with acquired immuno-deficiency syndrome (AIDS) and also by cancer and organ transplant patients. It has been estimated that some 65% of AIDS patients develop PCP. Amongst such patients the condition is life-threatening.

PCP infection in AIDS patients using pentamidine has been by intravenous infusion or intramuscular injection although this treatment is often accompanied by severe side-effects, eg hypotension, renal failure and hypoglycaemia. More recently, there has been reported (Abstracts of the Annual Meeting of the American Society of Microbiology 86, 14 (1986)) a method for the prevention of PCP which comprises the administration by inhalation of a nebulised aqueous solution of pentamidine.

A problem which has hitherto been encountered with the use of aqueous solutions of pentamidine is that such solutions, which have a pH in the range 4.5 to 6.5, are not stable and must therefore be made up immediately prior to use.

SUMMARY OF THE INVENTION

We have now found that aqueous solutions of pentamidine of reduced pH are stable and that, surprisingly, such solutions may be administered by inhalation to the lung.

Thus, according to the invention we provide a pharmaceutical composition comprising an aqueous solution of pentamidine or a pharmaceutically acceptable salt thereof (hereinafter referred to as the active ingredient), the solution having a pH of less than 4.5.

According to another aspect of the invention, there is provided a method for the prophylactic or remedial treatment of pneumo-cystis carinii pneumonia, which method comprises administration by inhalation to a patient having or being susceptible to that condition of a therapeutically effective quantity of an aqueous solution of pentamidine, or a pharmaceutically acceptable salt thereof, the solution having a pH of less than 4.5.

DETAILED DESCRIPTION OF THE INVENTION

The concentration of active ingredient in the solution may be from 0.1 to 10% w/v (measured as the free base). The concentration of active ingredient is, however, preferably less than 5%, and more preferably less than 3% eg 1% w/v.

Pharmaceutically acceptable salts of pentamidine which may be used include the isethionate, the naphthoate and the mesylate. We particularly prefer to use the isethionate.

The pH of the solution is preferably less than 4.0, more preferably less than 3.5, and especially less than 3.0.

The pH of the solution is preferably greater than 1.5, more preferably greater than 2.0 and especially greater than 2.5.

The pH of the solution may be adjusted by the addition of a pharmaceutically acceptable acid. Pharmaceutically acceptable acids which may be used include organic acids, eg acetic acid, and, more preferably, mineral acids, eg hydrochloric acid and sulphuric acid. A particularly preferred acid which may be used to adjust the pH is hydrochloric acid.

The solution may be buffered or, more preferably, non-buffered. Buffering agents which may be used will be readily apparent to those skilled in the art but, by way of example, the following may be mentioned:

sodium dihydrogen orthophosphate (sodium acid phosphate BP), di-sodium hydrogen phosphate (sodium phosphate BP) sodium citrate/citric acid, and boric acid/sodium borate.

The solution may be made isotonic with physiological fluids by the incorporation of a suitable tonicity agent eg sodium chloride. The solution may typically contain from about 0.1 to 1.0, more typically 0.5 to 1.0% w/v sodium chloride.

Other excipients which may be present in the solution include chelating or sequestering agents. Suitable chelating or sequestering agents include sodium carboxymethyl cellulose, citric, tartaric and phosphoric acids, and amino carboxylate compounds. The preferred chelating agent, however, is ethylenediamine tetraacetic acid or a salt thereof, especially the disodium salt.

The proportion and concentration of buffers, if included, and other excipients may be varied within fairly wide ranges, provided the resulting solution is stable and non-irritant when applied to the appropriate tissues. The maximum total concentration of excipients and buffers is preferably less than 5% w/v and more preferably less than 2% w/v.

The solutions of the invention may be made up, for example, by dissolving the active ingredient and excipients (if included) in freshly distilled water, adjusting the pH if necessary, making the solution up to the desired volume with distilled water, stirring and then sterilising. Sterilisation is preferably performed by sterile filtration into a previously sterilised container.

The solution is preferably made up at a temperature of from about 10° to 50° C., for example at room temperature.

The solution may be put up in unit dosage form, in which case preservatives may be incorporated, but are generally not necessary. Alternatively the solution may be put up in multi-dose form. In general it will be necessary to incorporate one or more preservatives into multi-dose solutions to ensure that the solution remains sterile after initial use.

The preferred preservative for solutions for inhalation is chlorbutol. The concentration of preservative should be such as to ensure effective preservation of the solution ie such that bacterial growth in the solution is inhibited. For most preservatives the concentration will typically lie in the range 0.001 to 0.1% w/v. However, in the case of chlorbutol acceptable concentrations are greater than 0.25% but less than 0.6% w/w ie the concentration of chlorbutol is 0.25 to 0.6%, preferably 0.3 to 0.55% eg 0.5% w/w.

Unit doses of the solutions of the invention for use in nebulisers may be packed in glass or plastics ampoules which are broken open immediately prior to use.

Multi-dose solutions may be packaged in volumes of 5 to 300 ml. Preferred volumes for inhalation compositions include 60, 120 and 240 ml.

We prefer multi-dose solutions to be packaged such that unit volumes of the solution to be administered can be accurately dispensed. The solution may, for example, be packaged in a flexible-walled container provided with a cap to receive the unit volume.

The required dose of active ingredient to be administered will vary with, amongst other factors, the severity of the condition being treated, and will depend on whether the treatment is remedial or prophylactic. For administration by intravenous infusion or intramuscular injection (generally for remedial treatment), a dose of about 4 mg/kg/day is administered for 14 to 21 days. For administration by these routes the solution of the invention would typically be diluted immediately before use. For administration to the lungs by nebulisation, a dose of from about 1 to 200 mg, preferably from 20 to 80 mg and especially about 40 mg is appropriate for prophylactic treatment. Each dose is typically administered weekly for 4 to 6 weeks and thereafter biweekly. For remedial treatment of PCP infection, more frequent dosage may be called for, eg 1 to 8 times (preferably 4 times) daily. This higher dosage regime may be maintained for as long as the infection persists (typically 7 to 21 days).

The aqueous solutions according to the present invention are advantageous in that they are more stable than are known solutions of the active ingredient.

The invention is illustrated, but in no way limited, by the following Examples.

Example 1

Non-preserved nebuliser solution

| Pentamidine isethionate | 1.0% w/v |
|---|---|
| Sodium chloride | 0.79 |
| Hydrochloric acid | q.s. |
| Purified water | to 100 |

Pentamidine isethionate (10 g) and sodium chloride (7.9 g) were dissolved in purified water (900 ml). The pH of the solution was adjusted to between 2.5 and 3.0 by addition of hydrochloric acid and the volume made up to 1000 ml with purified water.

The solution was sterile-filled into glass ampoules which were then sealed.

Example 2

Preserved nebuliser solution

| Pentamidine isethionate | 1.0% w/v |
|---|---|
| Sodium chloride | 0.79 |
| Chlorbutol | 0.5 |
| Hydrochloric acid | q.s. |
| Purified water | to 100 |

Chlorbutol (5 g) was dissolved in purified water (900 ml). Pentamidine isethionate (10 g) and sodium chloride (7.9 g) were then added to the solution. The pH of the solution was adjusted to between 2.5 and 3.0 by addition of hydrochloric acid and the volume made up to 1000 ml with purified water.

The solution was filled into polyethylene bottles of 120 ml capacity.

We claim:

1. A pharmaceutical composition comprising an aqueous solution of pentamidine or a pharmaceutically acceptable salt thereof, the solution having a concentration of active ingredient of 0.1 to 10% w/v and a pH greater than 1.5 and less than 4.5.

2. A composition according to claim 1, wherein the concentration of active ingredient in the solution is from 0.1 to 5% w/v.

3. A composition according to claim 1, wherein the concentration of active ingredient is from 0.1 to 3% w/v.

4. A composition according to claim 1, wherein the pH of the solution is less than 4.0.

5. A composition according to claim 1, wherein the pH of the solution is less than 3.5.

6. A composition according to claim 1, wherein the pH of the solution is less than 3.0.

7. A composition according to claim 1, wherein the pH of the solution is greater than 2.0.

8. A composition according to claim 1, wherein the pH of the solution is greater than 2.5.

9. A composition according to claim 1, wherein the pH of the solution is from 2.0 to 3.0.

10. A composition according to claim 1, wherein the solution contains from 0.1 to 1.0% w/v sodium chloride.

11. A composition according to claim 1, wherein the solution contains from 0.5 to 1.0% w/v sodium chloride.

12. A composition according to claim 1, wherein the active ingredient is pentamidine isethionate.

13. A method for the prophylactic or remedial treatment of pneumo-cystis carinii pneumonia, which method comprises administration by inhalation to a patient having or being susceptible to that condition of a therapeutically effective quantity for said treatment of an aqueous solution of pentamidine, or a pharmaceutically acceptable salt thereof, the solution having a pH of greater than 1.5 and less than 4.5.

14. A method according to claim 13, wherein the pH of the solution is less than 4.0.

15. A method according to claim 13, wherein the pH of the solution is less than 3.5.

16. A method according to claim 13, wherein the pH of the solution is less than 3.0.

17. A method according to claim 13, wherein the pH of the solution is from 2.0 to 3.0.

18. A method according to claim 13, wherein the solution contains pentamidine isethionate.

* * * * *